US00RE40876E

(19) United States
(12) Reissued Patent
Yakubu-Madus et al.

(10) Patent Number: US RE40,876 E
(45) Date of Reissued Patent: Aug. 18, 2009

(54) METHOD FOR TREATING NON-INSULIN DEPENDENT DIABETES USING THIAZOLIDINEDIONES WITH GLUCAGONLIKE PEPTIDE-1 AND AGONISTS THEREOF

(75) Inventors: Fatima Emitsel Yakubu-Madus, Indianapolis, IN (US); Lawrence Edward Stramm, Indianapolis, IN (US); Louis Vignati, Indianapolis, IN (US); William Terry Johnson, Cape Coral, FL (US)

(73) Assignee: Eli Lilly and Company, Indianapolis, IN (US)

(21) Appl. No.: 11/650,410

(22) PCT Filed: Jun. 6, 2000

(86) PCT No.: PCT/US00/15548

§ 371 (c)(1), (2), (4) Date: Apr. 24, 2001

(87) PCT Pub. No.: WO00/78333

PCT Pub. Date: Dec. 28, 2000

Related U.S. Patent Documents

Reissue of:
(64) Patent No.: 6,660,716
Issued: Dec. 9, 2003
Appl. No.: 09/830,323
Filed: Jun. 6, 2000

U.S. Applications:
(60) Provisional application No. 60/139,794, filed on Jun. 21, 1999.

(51) Int. Cl.
*A61K 38/00* (2006.01)
*A61K 31/50* (2006.01)

(52) U.S. Cl. ..... 514/2; 530/308; 530/300; 514/252.01

(58) Field of Classification Search ..... None
See application file for complete search history.

(56) References Cited

U.S. PATENT DOCUMENTS

| | | | |
|---|---|---|---|
| 5,545,618 | A | 8/1996 | Buckley et al. |
| 5,631,224 | A | 5/1997 | Efendic et al. |
| 2001/0047084 | A1 | 11/2001 | Knudsen et al. |

FOREIGN PATENT DOCUMENTS

| | | | |
|---|---|---|---|
| EP | 0 733 644 | A1 | 9/1996 |
| EP | 0 861 666 | A2 | 9/1998 |
| WO | WO 95/31214 | | 11/1995 |
| WO | WO 96/20005 | | 7/1996 |
| WO | WO 98/57636 | A | 12/1998 |
| WO | WO 99/03478 | | 1/1999 |
| WO | WO 99/43708 | | 9/1999 |
| WO | WO 00/00195 | A | 1/2000 |

OTHER PUBLICATIONS

Bowen L, Stein PP, Stevenson R, Shulman GI: "The Effect of CP68,722, a Thiazolidinedione Derivative, on Insulin Sensitivity in Lean and Obese Zucker Rats." Metabolism 40:1025–1030, 1991.

Chang Ay, Wyse BM, Gilchrist BJ, Peterson T, Diani AR: "Ciglitazone, a New Hypoglycemic Agent 1: Studies in OB/OB and DB/DB Mice, Diabetic Hamsters, and Normal and Streptozotocin–diabetic Rats." Diabetes 32:830–38, 1983.

Fujita T, Sugiyama Y, Taketomi S, Sohda T, Kawamatsu Y, Iwatsuka H, Suzuoki Z: "Reduction of Insulin Resistance in Obese and/or Diabetic Animals by 5–[4–(Methylcyclohexylmethoxy)benzyl}–thiazolidine–2, 4–dione (ADD–3878, U–63,287, Ciglitazone), a New Antidiabetic Agent." Diabetes 32:804–810, 1983.

Fujiwara T, Yoshioka S, Yoshioka T, Ushiyama I, Horikoshi H: "Characterization of New Oral Antidiabetic Agent CS–045 Studies in KK and OB/OB Mice and Zucker Fatty Rats." Diabetes 37: 1549–58, 1988.

Hvdberg A, Nielsen, T.M., Hilsted, J., Orskov, C., and Holst, J. J. "Effect of Glucagon–Like Peptide–1 (proglucagon 78–107 amide) on hepatic glucose production in healthy man." Metabolism, vol. 43, #1 Jan. 1994, pp. 104–108.

Iwamoto Y, Kuzuya T, Matsuda A, Awata T, Kumakura S, Inooka G, Shiraishi I: "Effect of New Oral Antidiabetic Agent CS–045 on Glucose Tolerance and Insulin Secretion in Patients with NIDDM." Diabetes Care 14: 1083–86, 1991.

Kraigen EW, James DE, Jenkins AB, Chisholm DJ, Storlien LH: "A Potent in Vivo Effect of Ciglitazone on Muscle Insulin Resistance Induced by High Fat Feeding of Rats." Metabolism 38: 1089–1093, 1989.

Kuzuya T, Iwamoto Y, Kosaka K, Yamanoushi T, Kasuga M, Kajinuma H, Akanuma Y, Yoshida S, Shigeta Y, Baba S: "A Pilot Clinical Trial of a New Oral Hypoglycemic Agent, CS–045, in Patients with Non–Insulin Dependent Diabetes Mellitus." Diabetes Res. And Clin Practice. 11:147–53, 1991.

(Continued)

*Primary Examiner*—Dong Jiang
(74) *Attorney, Agent, or Firm*—Caren D. Geppert; Gregory A. Cox; Mark J. Stewart

(57) ABSTRACT

Thiazolidinedione (TZD) and its pharmacologically active derivatives can be used in combination with agonists of glucagon-like peptide-1 (GLP-1), to treat non-insulin dependent diabetes mellitus, optionally with other therapies, by improving glycemic control while minimizing side effects, such as heart hypertrophy and elevated fed-state plasma glucose, which are associated with both TZD and GLP-1 monotherapies. Thus, the co-administration of TZD and GLP-1 helps regulate glucose homeostasis in Type II diabetic patients.

23 Claims, No Drawings

OTHER PUBLICATIONS

O'Rourke CM, Davis J, Saltiel AR, and Cornicelli JA: "Metabolic Effects of Troglitazone in the Goto–kakizaki rat, a Non–obese and Normolipidemic Rodent Model of Non–insulin–dependent Diabetes Mellitus." Metabolism 46: 192–198, 1997.

Reasner, C. A., II: "Promising New Approaches," Diabetes, Obesity Metab. (1999), 1 (Suppl. 1), pages S41–S48 XP–000971954.

Suter SL, Nolan JJ, Wallace P, Gumbiner B, Olefsky JM: "Metabolic Effects of New Oral Hypoglycemic Agent CS–045 in NIDDM Subjects." Diabetes Care, 15:193–203, 1992.

William GD, Delda A, Jordan WH, Gries C, Long GG, Dimarchi RD; "Subchronic Toxicity of the Thiazolidinedione, Tanabe–174 (LY 282449), in the Rat and Dog." Diabetes 42: 1993.

METHOD FOR TREATING NON-INSULIN DEPENDENT DIABETES USING THIAZOLIDINEDIONES WITH GLUCAGONLIKE PEPTIDE-1 AND AGONISTS THEREOF

Matter enclosed in heavy brackets [ ] appears in the original patent but forms no part of this reissue specification; matter printed in italics indicates the additions made by reissue.

This application claims the benefit of provisional application 60/139,794 filed Jun. 21, 1999.

BACKGROUND OF THE INVENTION

The present invention relates to a combination of a thiazolidinedione (TZD), with glucagon-like peptide-1 (GLP-1) or a GLP-1 agonist, which combination possesses desirable hormonal activity and can be used to regulate glucose homeostasis in patients suffering from non-insulin dependent diabetes mellitus (Type II diabetes).

Insulin resistance is a classic feature of many human disease conditions, such as Non-Insulin-Dependent Diabetes Mellitus (NIDDM), obesity, hypertension, aging, etc. Diabetes mellitus is a disorder of carbohydrate metabolism, characterized by hyperglycemia and glycosuria resulting from inadequate production or utilization of insulin. NIDDM is a form of diabetes where utilization of insulin is inadequate. It occurs predominantly in adults, in whom adequate production of insulin is available for use, yet a defect exists in insulin-mediated utilization and metabolism of glucose and peripheral tissues. For some people with diabetes, a mutation in the gene(s) coding for insulin, for insulin receptor and/or for insulin-mediated signal transduction factor(s) leads to ineffective insulin and/or insulin-mediated effects, impairing the utilization or metabolism of glucose.

Diabetes mellitus often develops from certain at risk populations; it is known that one such population is individuals with impaired glucose tolerance (IGT). The usual meaning of impaired glucose tolerance is that it is a condition intermediate between frank, non-insulin-dependent diabetes mellitus and normal glucose tolerance. IGT is diagnosed by a procedure wherein an effected person's postprandial glucose response is determined to be abnormal as assessed by two-hour postprandial plasma glucose levels. In this test, a measured amount of glucose is given to the patient and blood glucose level measured at regular intervals, usually every ½ hour for the first two hours and every hour thereafter. In a "normal" or non-IGT individual, glucose levels rise during the first two hours to a level less than 140 mg/dl and then drop rapidly. In an impaired individual (IGT) the blood glucose levels are higher and the drop-off level is at a slower rate. A high percentage of the impaired (IGT) population is known to progress to non-insulin dependent diabetes mellitus.

The pathophysiology of non-insulin-dependent diabetes mellitus (NIDDM) consists of three major components, (1) peripheral insulin resistance; (2) increased hepatic glucose production; and (3) impaired insulin secretion. Intense research has been devoted to each of these areas, independently, in order to determine which abnormality is primary and which are secondary. The prevailing view is that a rational therapeutic pharmacological approach should involve intervention in the insulin resistance to improve glucose homeostasis. Suter et al., *Diabetes Care* 15: 193–203 (1992). As a result of the focus on individual abnormalities, several model therapies were developed to regulate glucose homeostasis in Type II diabetic patients.

When focusing on peripheral insulin resistance, the drug of choice is a thiazolidinedione, which is a type of insulin-sensitizing agent. Troglitazone (TRG), for example, is an orally active anti-diabetic agent of the thiazolidinedione chemical series. This drug has been shown to reverse insulin resistance in patients with NIDDM and impaired glucose tolerance, and can enhance insulin action in numerous genetic and acquired rodent models of insulin resistance. The antihyperglycemic effects of TRG result from its ability to increase insulin dependent glucose disposal and reduce hepatic glucose production. It is believed, by enhancing insulin action, TRG treatment results in euglycemia at a lower circulating insulin level. In this regard, studies in normal and diabetic rodents and human clinical trials have not revealed hypoglycemia as a complication of thiazolidinedione therapy. On the other hand, administration of these drugs to normal or insulin-deficient diabetic animals failed to alter plasma glucose or insulin or glucose tolerance, although insulin sensitivity was nevertheless increased.

The effects of TRG and other thiazolidinediones on glucose disposal are thought to result from insulin sensitization, indicating an absolute requirement for insulin. On the other hand, TRG does improve insulin sensitivity as assessed by the hyperinsulinemic clamp. Suter et al., supra. Dose-dependent effects of thiazolidinediones on plasma insulin and glucose tolerance have been demonstrated in mouse and rat models other than the GK rat model.

Inhibiting gluconeogenesis in vivo would result in a decrease in glycogen stores. Following TRG treatment, we presumably begin with a smaller amount of glycogen and therefore show a decrease in total hepatic glucose output. It is also possible that TRG has a direct effect on the glycogenolitic pathway. The exact biochemical mechanism responsible for this effect is still under investigation. In vivo and ex vivo data in the GK rat further support the possibility that the effects of this drug on liver and peripheral tissue may be independent and different in some respects.

Thiazolidinedione treatments are based on the assumption that if you focus on peripheral insulin resistance, increased hepatic glucose production and impaired insulin secretion will be alleviated in due course. Additionally, determining the optimal dose of TZD for increasing insulin sensitivity has been a difficult undertaking. There is an additional dilemma that, even at the optimum dose, TZD monotherapy causes heart hypertrophy in animal models. Smits et al., *Diabetologia* 38:116–121 (1995). This side effect renders TZD monotherapy an undesirable prophylactic measure in the treatment of Type II diabetes mellitus.

The other primary approach to treating Type II diabetes mellitus focuses on facilitating insulin secretion, using insulin secretion-potentiating agents. The endocrine secretions of the pancreatic islets are under complex control not only by blood-borne metabolites (glucose, amino acids, catecholamines, etc.), but also by local paracrin influences. The major pancreatic islet hormones (glucagon, insulin and somatostatin) interact amongst their specific cell types (A, B and D cells, respectively) to modulate secretory responses mediated by the aforementioned metabolites. Although insulin secretion is predominantly controlled by blood levels of glucose, somatostatin inhibits glucose-mediated insulin secretory responses. In addition to the proposed inter-islet paracrin regulation of insulin secretion, there is evidence to support the existence of insulinotropic factors in the intestine. For example, glucose taken orally is a much more potent stimulant of insulin secretion than is a comparable amount of glucose given intravenously.

By focussing primarily on secretion of endogenous insulin, this method relies on the assumption that peripheral insulin resistance and increased hepatic glucose production would be regulated by insulin secretion treatments alone. However, of equal importance to the effective treatment of non-insulin diabetes mellitus is insulin sensitization which is the promotion of glucose utilization by enhanced insulin action. Increasing insulin secretion and/or synthesis without decreasing insulin resistance has little effect on glucose utilization.

Attempts to address the multiple abnormalities associated with non-insulin dependent diabetes mellitus have called for the co-administration of GLP-1 in conjunction with glibenclamide, which is a sulphonylurea. See U.S. Pat. No. 5,631,224. Sulphonylurea derivatives stimulate insulin secretion without an effect on insulin synthesis. Sulphonylureas act by closure of ATP-dependent potassium channels and pancreatic beta-cells. This leads to depolarization of the plasma membranes with opening of voltage-dependent calcium channels with inflow of calcium ions. Calcium ions bind to calmodulin, leading to activation of insulin exocytosis in a similar manner to that found after stimulation with glucose. In contrast to earlier beliefs, some sulphonylureas, such as glibenclamide, may interact with human vascular ATP-dependent channels. This may have consequences for vascular responses during ischaemia, which are, at least in part, mediated by ATP-dependent potassium channels.

During ischaemia in experimental animals, it has been suggested that shortening of the action potential exerts a protection effect, thereby reducing contractility, oxygen demand and repercussion damage. Under these circumstances sulphonylureas such as glibenclamide may inhibit potassium channels in the ischaemic myocardium, and so prevent the shortening of the action potential. This may result in less coronary vasodilation, more tissue damage and more reperfusion arrhythmias.

In light of heart hypertrophy, which is a side effect of TZD and increased tissue damage resulting from sulphonylurea administration, a new approach to treating type II diabetes mellitus is needed. The new approach should be a multi-pronged approach to the pathophysiology of NIDDM, which is not limited to the treatment of only peripheral insulin resistance, or only impaired insulin secretion. The appropriate treatment would ameliorate peripheral insulin resistance, increase hepatic glucose production, and facilitate insulin secretion without heart hypertrophy and increased tissue damage.

SUMMARY OF THE INVENTION

It therefore is an object of the present invention to provide for the synergistic use of thiazolidinediones and glucagon-like peptide-1 agonists, to treat metabolic instability associated with non-insulin dependent diabetes mellitus.

It is another objective of the present invention to provide a method for treating non-insulin dependent diabetes mellitus.

In accomplishing these and other objectives, there has been provided, in accordance with one aspect of the present invention, a therapeutic method comprised of co-administering a pharmacologically effective dose of an insulin secretion-potentiating agent, such as an incretin hormone, and a thiazolidinedione, such that blood glucose levels are decreased and insulin secretion is increased. In a preferred embodiment, the invention includes co-administration of an effective dosage of a thiazolidinedione, such as troglitazone, and a glucagon-like peptide-1 or a glucagon-like peptide-1 agonist, as an insulin secretion-potentiating agent.

Thiazolidinediones can be used, in combination with agonists of glucagon-like peptide-1, to treat non-insulin dependent diabetes mellitus, optionally with other therapies, by improving glycemic control while minimizing side effects, such as heart hypertrophy, tissue damage and elevated fed-state plasma glucose, which are associated with TZD and GLP-1 monotherapies.

The invention includes a method of treating non-insulin dependent diabetes mellitus, comprising co-administering an effective dosage of (a) an incretin hormone (b) a thiazolidinedione. The incretin hormone used in this method may be a glucagon-like peptide-1 molecule, for example a GLP-1 analog. Accordingly, the invention includes this method of treating, where the incretin hormone is an agonist selected from the group consisting of Glucagon-Like Peptide-1(7-37)OH, Glucagon-Like Peptide-1(7-36)amide, $VAL^8$-GLP-1(7-37), $GLY^8$-GLP-1(7-37), $THR^8$-GLP-1(7-37), $MET^8$-GLP-1(7-37), and $IP^7$. The TZD used in the method of the invention may be selected from the group consisting of pioglitazone, troglitazone, rosiglitazone and TZD 300512.

In another embodiment, the invention includes a method of treating non-insulin dependent diabetes mellitus, comprising co-administering an effective dosage of (a) an incretin hormone (b) a thiazolidinedione, where the effective dosage of the incretin hormone is in the range of about 20 to about 100 μg per day. In another embodiment, the effective dosage of the TZD is in the range of about 0.1 to about 200 milligrams per day In another embodiment, the insulin secretion-potentiating agent and the TZD are administered simultaneously, in a method of treating non-insulin dependent diabetes mellitus, comprising co-administering an effective dosage of (a) an incretin hormone (b) a thiazolidinedione. In yet another embodiment of a method of treating NIDDM, the incretin hormone and the TZD are administered sequentially.

The present invention also includes a method of treating non-insulin dependent diabetes mellitus, comprising co-administering an effective dosage of (a) a thiazolidinedione and (b) a glucagon-like peptide-1 agonist, such that blood glucose levels are decreased and insulin secretion is increased.

The invention also includes an insulinotropic formulation comprising (a) an incretin hormone, (b) a TZD, and (c) a pharmaceutically acceptable carrier. In another embodiment, the incretin hormone of the inventive formulation is a glucagon-like peptide-1 molecule. In yet another embodiment, the formulation comprises an incretin hormone that is an agonist selected from the group consisting of Glucagon-Like Peptide-1(7-37)OH, Glucagon-Like Peptide-1(7-36)amide, $VAL^8$-GLP-1(7-37), $GLY^8$-GLP-1(7-37), $THR^8$-GLP-1(7-37), $MET^8$-GLP-1(7-37), and $IP^7$. In another embodiment, the insulinotropic formulation of the invention comprises a TZD selected from the group consisting of pioglitazone, troglitazone, rosiglitazone and TZD 300512.

The invention also includes a composition of matter comprising (i) a container suitable for holding a solution to be infused in a patient, (ii) a liquid preparation comprising an amount of an incretin hormone in a pharmaceutically acceptable carrier such that said preparation represents an incretin hormone dosage of between about 5 to about 200 μg per day and (iii) instructions on infusing a patient with said preparation, said patient suffering from non-insulin dependent diabetes mellitus, such that said patient receives an infusion of said dosage of said preparation. In another embodiment of the invention, the instructions in the composition further direct administering a therapy to said patient prior to or concomitantly with said infusing, said therapy targeting a specific disease state. In one embodiment, the incretin hormone of the composition of the invention is a glucagon-like peptide-1 molecule. In another embodiment, the incretin hormone of the composition is an amide agonist selected from the group consisting of Glucagon-Like Peptide-1(7-37)OH, Glucagon-Like Peptide-1(7-36)amide, $VAL^8$-GLP-1(7-37), $GLY^8$-GLP-1(7-37), $THR^8$-GLP-1(7-37), $MET^8$-GLP-1(7-37), and $IP^7$.

In another embodiment, the invention includes a composition of matter comprising (i) a container suitable for holding a solution to be infused in a patient, (ii) a liquid preparation comprising an amount of an incretin hormone in a pharmaceutically acceptable carrier such that said preparation represents an incretin hormone dosage of between about 20 to about 200 μg per day and (iii) instructions on infusing a patient with said preparation, said patient suffering from non-insulin dependent diabetes mellitus, such that said patient receives an infusion of said dosage of said preparation, and (iv) a second preparation comprising an amount of a TZD in a pharmaceutically acceptable carrier such that said second preparation represents a TZD dosage of between about 0.1 to about 200 milligrams per day. In another embodiment, the second preparation is a liquid. In yet another embodiment, the TZD in the composition is selected from the group consisting of pioglitazone, troglitazone, rosiglitazone and TZD 300512.

The invention also includes a composition of matter comprising (i) a container suitable for holding a solution to be infused in a patient, (ii) a liquid preparation comprising an amount of an incretin hormone in a pharmaceutically acceptable carrier such that said preparation represents an incretin hormone dosage of between about 20 to about 200 μg per day and (iii) instructions on infusing a patient such that said patient's blood glucose level is decreased and insulin secretion is increased.

DETAILED DESCRIPTION OF PREFERRED EMBODIMENTS

In accordance with the present invention, TZD and its pharmacologically active derivatives can be used, in combination with GLP-1 and its agonists, to treat non-insulin dependent diabetes by improving glycemic control while minimizing side effects, such as heart hypertrophy and elevated fed-state plasma glucose, which are associated with both TZD and GLP-1 monotherapies. This therapeutic approach can be employed with other therapies which utilize, for example, proteins, sulphonylureas, biguanides, and/or 2-glucosidase inhibitors, to improve glycemic control and to minimize the side effects associated with individual therapies.

Thiazolidinediones and GLP-1 agonists have undergone evaluation for efficacy in treating type II diabetes. Thiazolidinediones have been shown, in several insulin-resistant type II animal models, to alter carbohydrate and glucose metabolism favorably, ameliorating insulin resistance. In addition to increasing insulin sensitivity, TZD also causes heart hypertrophy at optimal doses in animal models. By contrast, GLP-1 agonists, such as $IP^7$, are anti-diabetic due to their glucose-dependent insulin-releasing activity. In recent studies in type II diabetic patients, infusion of GLP-1 reduced post-meal glucose excursions, reduced meal-related insulin requirements, and lowered glucagon levels; however, increased tissue damage resulted.

As demonstrated in the present specification, the synergistic use of a TZD, and a GLP-1 agonist, has led to favorably unexpected results. Studies were designed to evaluate the effects of a GLP-1 agonist and a TZD, as a combination therapy, on glucose metabolism, and on occurrence of heart hypertrophy associated with TZD monotherapy, in diabetic rats. The data showed that the heart hypertrophy associated with TZD monotherapy was prevented when a TZD was administered in conjunction with a GLP-1 agonist. The improvement was statistically significant, using a T-test. Thus, this novel method prevented the cardiovascular effects associated with insulin-stimulating agents Furthermore, as detailed herein, the plasma glucose levels of diabetic rats treated with GLP-1 and TZD monotherapies increased over a 42-day treatment period. In contrast, when a TZD and GLP-1 were co-administered, rats showed a slight decrease in plasma glucose levels followed by a steady-state level over the course of the 42-day treatment. Thus, the novel combination therapy of the present invention enhances glycemic control, but does not cause heart hypertrophy, in diabetic rats.

Accordingly, the co-administration of a TZD and a GLP-1 molecule should augment regulation of glucose homeostasis in human NIDDM patients, without the side effects associated with insulin secretion-potentiating and insulin-sensitizing agents.

I. TERMS

The following terms are used in this application:

Co-administration—As used in this application, "co-administration" means the administration of two or more compounds to the same patient, within a time period of up to about three to about four hours. For example, co-administration encompasses (1) simultaneous administration of a first and second compound; (2) administration of a first compound, followed by administration of a second compound about 2 hours after administration of the first compound; and (3) administration of a first compound, followed by administration of a second compound about 4 hours after administration of the first compound. As described herein, the present invention encompasses co-administration of a TZD and a GLP-1 molecule to a patient suffering from non insulin-dependent diabetes mellitus.

Insulin secretion-potentiating agent: Any compound, which stimulates the secretion of insulin whether the compound has an effect on insulin synthesis, or not. The most common mechanism by which these compounds stimulate insulin is by various effects on ATP-dependent potassium channels in pancreatic-beta cells. Insulin secretion-potentiating agents are typically sulphonylureas, non-sulphonylurea insulin secretagogues, or incretin hormones.

Incretin hormone: Any hormone that is released after meals and potentiates insulin secretion during the post-prandial phase. Examples of such a hormone include GIP (gastric inhibitory peptide), GLP-1(7-36) and GLP-1 (7-37).

Glucagon-Like Peptide-1 (GLP-1): An insulinotropic fragment of the proglucagon molecule. Two shorter forms of GLP-1, the (7-37) and (7-36) amides, are strong glucose-dependent stimulators of insulin secretion, as demonstrated in vitro and in vivo.

Insulinotropic: The ability of a substance to stimulate or cause the stimulation of, the synthesis, expression and/or mobilization of the hormone insulin.

Thiazolidinediones (TZDs): A class of compounds which work by enhancing insulin action and promoting glucose utilization in peripheral tissue. TZDs include compounds known in the art as "TZD derivatives." TZDs have no effect on insulin secretion. They apparently work by enhancing insulin action and thus promoting glucose utilization in peripheral tissues, possibly by stimulating non-oxidative glucose metabolism in muscle, and suppressing gluconeogenesis in the liver. The chemical compounds that comprise the Thiazolidinedione (TZD) class of compounds is exceptionally large. See, for example, Bowen, et al. *Metabolism* 40:1025 (1991); Chang, et al *Diabetes* 32:630 (1983); Colca, et al. *Metabolism* 37:276 (1988); Diani, et al. *Diabetologia*27:225 (1984); Fujita, et al. *Diabetes* 32:804 (1983); Fujiwara, et al. *Diabetes* 37:1549 (1988). Exemplary of the family of thiazolidinediones are troglitazone, ciglitazone, pioglitazone (see U.S. Pat. Nos. 4,687,777 and 4,287,200), englitazone, CS-045[(±)-5[4-(6-hydroxy-2,5,7,8-tetramethylchroman-2-YL-methoxy)benzyl]-2,4-thiazolidinedione], TZD 300512, and BRL 49653.

Preferred TZDs of the present invention include pioglitazone, troglitazone, rosiglitazone, and TZD 300512.

Preparation: The formulation of the active compound with encapsulating material as a carrier providing a capsule in which the active component with or without other carriers, is surrounded by a carrier, which is thus in association with it. This includes tablets, powders, capsules, pills, cachets, and lozenges which can be used as solid dosage forms suitable for oral administration.

Effective dosage: An effective dosage is the amount of a compound that prevents or ameliorates adverse conditions or symptoms of disease(s) or disorder(s) being treated. With respect to thiazolidinediones, effective dosage means a pharmacological dose in the range of about 0.1 mg/day to about 200 mg/day. A preferred dosage range is about 50 mg/day to about 200 mg/day. The skilled artisan will understand and appreciate that the effective dosage of a given TZD will vary with the potency of the TZD. With respect to GLP-1 molecules and other insulin-secretion potentiating agents, effective dosage is in the range of about 20 to about 100 μg/day. The preferred range is about 30 to about 50 μg/day. The skilled artisan will understand and appreciate that the effective dosage of a given GLP-1 molecule will depend on the potency of the particular molecule that is used.

II. GLP-1 MOLECULES

Glucagon-like peptide-1 (GLP-1) and analogs thereof potentiate insulin secretion, and have been suggested to save an effect on glucose utilization in peripheral tissues. GLP-1 and analogs thereof are known in the art. See, for example, U.S. Pat. No. 5,705,483. As used in the present specification, the term "GLP-1 molecule" refers to naturally-occurring GLP-1 (7-36)$NH_2$, GLP-1 (7-37), natural and unnatural functional analogs, variants, and derivatives thereof, and salts thereof. These molecules are described in more detail below.

The human hormone glucagon is a 20-amino acid peptide hormone produced in the A-cells of the pancreas. The hormone belongs to a multi-gene family of structurally related peptides that include secretion, gastric inhibitory peptide, a vasoactive intestine peptide and glicentin. These peptides variously regulate carbohydrate metabolism, gastrointestinal mobility and secretory processing. The principle recognized actions of pancreatic glucagon, however, are to promote hepatic glycogenolysis and glyconeogenesis, resulting in an elevation of blood sugar levels. In this regard, the actions of glucagon are counter regulatory to those of insulin and may contribute to the hyperglycemia that accompanies diabetes mellitus. Lund et al., *Proc. Natl. Acad. Sci.* USA 79: 345–49 (1982).

Glucagon has been found to be capable of binding to specific receptors, which lie on the surface of insulin producing cells. Glucagon, when bound to these receptors, stimulates the rapid synthesis of cAMP by these cells. cAMP, in turn, has been found to stimulate insulin expression Korman et al., *Diabetes* 34:717–722 (1985). Insulin acts to inhibit glucagon synthesis, Ganong, *Review of Medical Physiology* 273 (1979). Thus, the expression of glucagon is carefully regulated by insulin, and ultimately by the serum glucose level.

The glucagon gene is initially translated from a 360 base pair precursor to form the polypeptide preproglucagon, Lund et al., *Proc. Natl. Acad. Sci.* U.S.A. 79:345–349 (1982). This polypeptide is subsequently processed to form proglucagon. Patzlet et al., *Nature* 282:260–266 (1979), demonstrated that proglucagon was subsequently cleaved into glucagon in a second polypeptide. Subsequent work by Lund et al., Lopez et al., *Proc. Natl. Acad. Sci. U.S.A.* 80:5485–5489 (1983), and Bell et al., *Nature* 302:716–718 (1983), demonstrated that the proglucagon molecule was cleaved immediately after lysine-arginine dipeptide residues. Studies of proglucagon produced by channel catfish (ictalurus punctala) indicated that glucagon from this animal was also proteolytically cleaved after advanced lysine-arginine dipeptide residues, Andrews et al., *J. Biol. Chem.* 260:3910–3914 (1985), Lopez et al., *Proc. Natl. Acad. Sci. U.S.A.*, 80:5485–5489 (1983).

Bell et al., supra, discovered that mammalian proglucagon was cleaved at lysine-arginine or arginine-dipeptides, and demonstrated that the proglucagon molecule contained three discrete and highly homologous peptide molecules which were designated glucagon, glucagon-like peptide 1 (GLP-1) and glucagon-like peptide 2 (GLP-2). Lopez et al., concluded that GLP-1 was 37 amino acid residues long and that GLP-2 was 35 amino acid residues long. Analogous studies on the structure of rat preproglucagon revealed a similar pattern of proteolytic cleavage between adjacent lysine-arginine or arginine-arginine dipeptide residues, resulting in the formation of glucagon, GLP-1 and GLP-2 Heinrich et al., *Endocrinology* 115:2175–2181 (1984). Human, rat, bovine and hamster sequences of GLP-1 have been found to be identical Ghiglione et al., *Diabetologia* 27:599–600 (1984).

The conclusion reached by Lopez, et al., regarding the size of GLP-1 was confirmed by the work of Uttenthal et al., *J. Clin. Endocrinol. Metabol.* 61:472–479 (1984). Uttenthal et al., examined the molecular forms of GLP-1 which were present in the human pancreas. The research shows that GLP-1 and GLP-2 are present in the pancreas as 37 amino acid and 34 amino acid peptides, respectively.

The similarity between GLP-1 and glucagon suggested to early investigators that GLP-1 might have biological activity. Although some investigators found that GLP-1 could induce rat brain cells to synthesize cAMP Hoosein et al., *FEBS Lett.* 178:83–86 (1984), other investigators failed to identify any physiological role for GLP-1, Lopez et al., supra. The failure to identify any physiological role for GLP-1 caused some investigators to question whether GLP-1 was in fact a hormone and whether the relatedness between glucagon and GLP-1 might be artifactual.

It is now known that the various disclosed forms of GLP-1 are known to stimulate insulin secretion (insulinotropic action) and cAMP formation, see, e.g., Mojsov, *Int. J. Peptide Protein Research* 40:333–343 (1992). More importantly, multiple authors have demonstrated the nexus between laboratory experimentation and mammalian, particularly human, insulinotropic responses to exogenous administration of GLP-1, particularly, GLP-1 (7-36) $NH_2$ and GLP-1 (7-37), see, e.g., Nauck et al., *Diabetologia* 36:741–744 (1993); Gutniaket al., *New England J. of Medicne* 326 (20):1316–1322 (1992); Nauck et al., *J. Clin. Invest.* 91:301–307 (1993); and Thorenes et al., *Diabetes* 42:1219–1225 (1993).

GLP-1 (7-36)$NH_2$ is well known in the art, but is presented here as a convenience to the reader: $His^7$-Ala-Glu-$Gly^{10}$-Thr-Phe-Thr-Ser-$Asp^{15}$-Val-Ser-Ser-Tyr-$Leu^{20}$-Glu-Gly-Gln-Ala-$Ala^{25}$-Lys-Glu-Phe-Ile-$Ala^{30}$-Trp-Leu-Val-Lys-$Gly^{35}$-Arg-$NH_2$ (SEQ ID NO:1).

For GLP-1 (7-37), the carboxy-terminal amide functionality of $Arg^{36}$ is displaced with Gly at the 37th position of the GLP-1 (7-36)$NH_2$ molecule. In addition, the existence and preparation of a multitude of protected, unprotected, and partially protected natural and unnatural functional analogs and derivatives of GLP-1 (7-36)$NH_2$ and GLP-1 (7-37) molecules have been described in the art. See, for example, U.S. Pat. Nos. 5,120,712 and 5,118,666; and Orskov, C., et al., *J. Biol. Chem.*, 264(22):12826 (1989) and WO 91/11457 (Buckley, D. I., et al., published Aug. 8, 1991).

Variants of GLP-1 (7-37) and analogs thereof also have been disclosed. These variants and analogs include, $GLN^9$-GLP-1 (7-37), D-$GLN^9$-GLP-1 (7-37), acetyl $LYS^9$-GLP-1 (7-37), $THR^{16}$-$LYS^{16}$-GLP-1 (7-37), $LYS^{18}$-GLP-1 (7-37, GLP (7-37) OH (a/k/a IL7), and the like, and derivatives thereof including, for example, acid addition salts, carboxylate salts, lower alkyl esters, and amides. See, for example, WO91/11457. Preferred GLP-1(7-37) analogs of the present invention include $VAL^8$-GLP-1(7-37), $GLY^8$-GLP-1(7-37), $THR^8$-GLP-1(7-37), $MET^8$-GLP-1(7-37), and $IP^7$. "$IP^7$" is a GLP-1 analog that is 4-imidazopropionyl-GLP-1 (7-37)OH. Throughout this specification, this 4-imidazo compound is referred to as "$IP^7$-GLP-1(7-37)OH" or "$IP^7$". This analog is actually desaminohistidyl at the 7 position (amino terminus) of GLP-1(7-37)OH. This compound, and its synthesis, is described in U.S. Pat. No. 5,512,549.

III. NOVEL COMPOSITIONS OF THE INVENTION

The fundamental defects identified as causing hyperglycemia and non-insulin dependent diabetes are impaired secretion of endogenous insulin and resistance to the effects of insulin by muscle and liver, see Galloway, *Diabetes Care* 13:1209–1239 (1990). The latter defect results in excess production of glucose by the liver. Thus, whereas a normal individual releases glucose at the rate of approximately 2 mg/kg/minute, in patients with non-insulin dependent diabetes, this amount usually exceeds 2.5 mg/kg/minute, resulting in a net excess of at least 70 grams of glucose per 24 hours. Because there exists an exceedingly high correlation between hepatic glucose production, fasting blood glucose and overall metabolic control (as assessed by glycohemoglobin levels), Galloway, supra; and Galloway et al., *Clin. Therap.* 12:460–472 (1990), it was apparent to researchers that control of the fasting blood glucose is a sine qua non for achieving overall normalization of metabolism sufficient to prevent the complication of hyperglycemia. In view of the fact that present forms of insulin rarely normalize hepatic glucose production without producing significant hyperinsulinemia and hypoglycemia, Galloway and Galloway et al., supra, alternative approaches are needed.

The present invention relates to the unexpected discovery that co-administration of a TZD and a GLP-1 molecule exerts synergistic beneficial effects on glucose levels, insulin levels, and heart weight, in diabetic mammals. As discussed herein, "co-administration" means the administration of two or more compounds to the same patient, within a time period of up to about three to about four hours.

Pharmaceutical formulations of the TZD and GLP-1 molecules can be prepared according to known methods. The GLP-1 molecule and the TZD can be prepared together or preferably in separate steps. The preferred route of administering the GLP-1 molecule is parenteral administration. The preferred route of administering the TZD is mucosal administration, most preferably oral administration. However, it is possible to administer both the GLP-1 molecule and the TZD via parenteral administration. If a TZD is administered parenterally, the skilled artisan will understand and appreciate that those techniques described below for preparing a GLP-1 molecule can be used to prepare a parenteral formulation of a TZD.

A. Insulin-secretion potentiating agent

The insulin secretion-potentiating agent, such as an incretin hormone, is combined in admixture with a pharmaceutically acceptable carrier vehicle. Suitable vehicles and their formulation, inclusive of other human proteins, such as human serum albumin, are described in Remington's PHARMACEUTICAL SCIENCES, $16^{th}$ ed. (1980), for example. In order to form a pharmaceutically acceptable composition suitable for effective administration, such compositions will contain an effective amount of an agent, such as a GLP-1 molecule, together with a suitable amount of carrier vehicle.

Compositions containing a GLP-1 molecule may be administered intravenously, intramuscularly, subcutaneously or by pulmonary routes, such as inhalation. Dosages may be in the in the range of from about 20 to about 100 μg/day, although a lower or higher dosage may be administered, if appropriate. A preferred dosage range for a GLP-1 molecule is about 30 to about 50 μg/day. The required dosage may depend upon the severity of the condition of the patient and upon such criteria as the patient's height, weight, sex, age, and medical history.

For the purpose of parenteral administration, compositions containing a GLP-1 molecule are dissolved in distilled water and the pH-value is adjusted to about 6 to 8. In order to facilitate the lyophilization process resulting in a suitable product, a sugar such as lactose could be added to the solution. The solution is then filter sterilized, introduced into vials, and lyophilized. The concentration of the GLP-1 molecule in these compositions may vary from $10^{-12}$ M to $10^{-5}$ M.

Additional pharmaceutical methods may be employed to control the duration of action. Controlled release preparations may be achieved by the use of polymers to complex or absorb GLP-1 molecules. The controlled delivery may be exercised by selecting appropriate macromolecules, such as polyesters, polyamino acids, polyvinyl pyrrolidone, ethylenevinylacetate, methycellulose, carboxymethylcellulose and proamine sulfate, and the concentration of macromolecules, as well as the methods of incorporation of macromolecules, in order to control release. Another approach for controlling the duration of action via controlled release entails incorporating GLP-1 molecules into particles of a polymeric material, such as a polyesters, a polyamino acid, a hydrogel, a polylactic acid, or an ethylene vinylacetate polymer. Alternatively, it is possible to entrap a GLP-1 molecule in microcapsules prepared, for example, by coacervation techniques or by interfacial polymerization, for example, hydoxymethylcellulose or gelatin-microcapsules, respectively, or in colloidal drug delivery systems, for example, liposomes, albumin microspheres, microemulsions, nanoparticles, and nanocapsules or in macroemulsions. Such teachings are disclosed in Remington's PHARMACEUTICAL SCIENCES, supra.

B. TZDs

For preparing pharmaceutical compositions from a TZD, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired. The powders and tablets preferably contain from five or ten to about seventy percent of the active compound. Suitable carriers are magnesium carbonate, magnesium stearate, talc, sugar, pectin, dextrin, starch, gelatin, tragacanth, methylcellulose, sodium carboxymethylcellulose, a low melting wax, cocoa butter, and the like.

For preparing suppositories, a low melting wax, such as mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methycellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit, dosage form can be a capsule, tablet, cachet, or lozenge itself, or it can be the appropriate number of any of these in packaged form.

The quantity of active component in a unit dose preparation may be varied or adjusted from about 50 μg to about 100 mg, more usually from about 1 mg to about 10 mg of the active ingredient, according to the particular application and the potency of the active compound. The composition can, if desired, also contain other compatible therapeutic agents, in addition to a TZD.

Dosages may be in the in the range of from about 0.1 to about 200 mg/day, although a lower or higher dosage may be administered, if appropriate. A preferred dosage range for a TZD is about 50 to about 200 mg/day. The required dosage may depend upon the severity of the condition of the patient and upon such criteria as the patient's height, weight, sex, age, and medical history.

C. Co-Administration

The present invention contemplates using TZD and TZD derivatives in combination with GLP-1 agonists, to regulate glucose homeostasis in type II diabetes patients. This therapeutic approach can be employed with other therapies, using proteins, sulphonylureas, biguanides, and/or 2-glucosidase inhibitors, for example, to improve glycemic control and to minimize the side effects associated with individual therapy.

More generally, the present invention will find application in the treatment of at-risk individuals, such as those with impaired glucose tolerance, to prevent, delay or treat the onset of NIDDM and complications arising therefrom. To these ends, compounds are co-administered, as described above, either together or in a stepwise fashion, along with a pharmaceutically acceptable carriers at the initial dosage of about 0.1 to about 200 mg/day of the TZD and about 20 to 100 μg/day of the insulin secretion-potentiating agent. A preferred daily dosage range is about 50 to about 200 mg/day for the TZD and about 30 to about 50 μg/day of the insulin secretion-potentiating agent. The dosages may be varied, however, depending upon the requirements of the patient, the severity of the condition being treated, and the particular compounds employed.

Thus, determination of the proper dosage for a particular situation is within the skill of the art. In general, treatment is initiated with smaller dosages which are less than the optimum dose of the compounds. Thereafter, the dosage is increased by small increments until the optimum effect under the circumstances is reached. For convenience, the total daily dosage may be divided and administered in portions during the day, if desired.

The features disclosed in the present description, examples and claims, both separately and in combination thereof, are material for realizing this invention and diverse forms thereof. The invention is further illustrated by the following examples, which are not to be construed as limiting, but merely as an illustration of some preferred features of the invention.

EXAMPLE 1

Synergistic Effect of a TZD Derivative and GLP-1 Molecule Co-Administration on Heart Weight, Blood Glucose and Insulin Levels Thiazolidinediones have been shown in several insulin resistant type II animal models to favorably alter carbohydrate and lipid metabolism, ameliorating insulin resistance. TZD300512(TZD) is a potent thiazolidinedione. See European Patent Application EP 0 177 353. In addition to increasing insulin sensitivity, TZD also increases body weight and causes heart hypertrophy at optimal doses. In contrast, GLP-1(7-37)OH is antidiabetic due to its potent glucose-dependent insulin-releasing activity. In recent studies in Type II diabetic patients, infusion of GLP-1 reduced both post-meal glucose excursions, reduced meal-related insulin requirements, and lowered glucagon levels.

This study was designed to evaluate the effects of using a combination of sub-optimal doses of a TZD and a GLP-1 agonist on glucose metabolism and in addition, if this combination therapy would prevent occurrence of heart hypertrophy that is associated with optimal doses of TZD derivatives. Eight week old Zucker Diabetic Fatty (Genetic Models, Inc.) rats (ZDF) weighing about 350 grams were used in this study. Animals were allowed free access to water, and Purina Formulab 5008 chow. TZD 300512 was administered as 0.00006% diet admixture while $IP^7$-GLP-1 (7-37)OH, a GLP-1 agonist, was infused subcutaneously at a constant rate of 0.06 μg/min via implanted Aztet pumps. The duration of study was seven weeks, and food consumption and body weight were monitored daily. Plasma glucose and insulin levels were measured weekly, and Glycated hemoglobin A1c was measured at the end of the study. Heart weights also were measured at the end of the study.

The data from these studies, which is summarized in Table 1, demonstrates enhanced glucose control in the ZDF rat with co-administration of suboptimal doses of $IP^7$ and TZD without causing heart hypertrophy. Table 1 summarizes final rat weight, daily food intake, plasma glucose levels, plasma insulin levels, Hbalc, and heart weight. Values were rounded off to the nearest decimal point. Overall, the data in Table 1 demonstrates enhanced glycemic control without an increase in heart size at sub-optimal doses of TZD and GLP-1 agonist combination therapy.

with insulin-stimulating agents. For example, see Smits et al., *Diabetologia* 38: 116–121 (1995).

In contrast to the diabetic rat control, glucose levels were lowest in the TZD/$IP^7$ group. In particular, the fed state plasma-glucose levels of diabetic rats treated with TZD and GLP-1 agonist monotherapy were 51.6% and 57.5% of control levels, respectively, over a 42-day treatment period. In contrast, glucose levels in rats treated with TZD and GLP-1 co-administration were 26% of control levels, which demonstrates a significant improvement in plasma glucose control. Furthermore, during these experiments, a slight decrease in plasma glucose levels was observed, followed by a steady-state level over the course of the 42-day treatment.

Finally, compared to the non-treated groups, insulin levels were preserved in the groups treated with TZD, suggesting prevention of deterioration of beta cells with therapy.

The present invention may be embodied in other specific forms without departing from its spirit of its central characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

SEQUENCE LISTING

```
<160> NUMBER OF SEQ ID NOS: 1

<210> SEQ ID NO 1
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

TABLE 1

Summary of Data

| | Control | TZD | TZD + $IP^7$ | $IP^7$ |
|---|---|---|---|---|
| Weight (g) | 414.6 ± 8.2 | 510.7 ± 13.5 | 498.4 ± 5.8 | 424.7 ± 7.9 |
| Food Int (g/d) | 37.9 ± 1.7 | 37.3 ± 1.4 | 34.3 ± 0.9 | 30.4 ± 1.2 |
| Glucose (mg/dl) | 639.2 ± 29 | 330.0 ± 60.5 | 166.2 ± 13.3 | 367.5 ± 58.0 |
| Insulin (ng/ml) | 4.61 ± 1.2 | 19.7 ± 3.4 | 19.9 ± 1.5 | 13.0 ± 2.9 |
| Hbalc (%) | 12.9 ± 0.3 | 8.2 ± 1.1 | 5.0 ± 0.21 | 9.5 ± 1.0 |
| Heart wt (g) | 1.2 ± 0.5 | 1.3 ± 0.5 | 1.2 ± 0.01 | 1.2 ± 0.03 |

Heart weight was not significantly increased in the TZD/$IP^7$ group, compared to the control group, and heart weight in the TZD/$IP^7$ group was lower than in rats treated with TZD alone. Therefore, the heart hypertrophy associated with TZD monotherapy was prevented when TZD was administered in conjunction with a GLP-1 agonist. Moreover, there were none of the adverse cardiovascular effects associated

What is claimed is:

1. A method of treating non-insulin dependent diabetes mellitus comprising co-administering:

a) an effective dosage of a [GLP-1 peptide agonist] *GLP-1 molecule*; and b) an effective dosage of pioglitazone or rosiglitazone.

2. The method of claim 1 wherein an effective dosage of pioglitazone is administered.

3. The method of claim 1 wherein an effective dosage of rosiglitazone is administered.

[4. The method of claim 1 wherein the GLP-1 agonist is a GLP-1 molecule.]

5. The method of claim [4] *1* wherein the GLP-1 molecule is an analog of SEQ ID NO:1.

[6. The method of claim 5 wherein the effective dosage of the GLP-1 molecule is in the range of about 5 to about 200 μg per day.]

[7. The method of claim 5 wherein the effective dosage of the GLP-1 molecule is in the range of about 20 to about 100 μg per day.]

[8. The method of claim 5 wherein the effective dosage of the GLP-1 molecule is in the range of about 30 to about 50 μg per day.]

[9. The method of claim 5 wherein the effective dosage of pioglitazone or rosiglitazone is in the range of about 0.1 mg to about 200 mg per day.]

[10. The method of claim 5 wherein the effective dosage of pioglitazone or rosiglitazone is in the range of about 50 mg to about 200 mg per day.]

11. The method of claim [4] *1* wherein the GLP-1 molecule is a GLP-1 derivative.

12. The method of claim 11 wherein the effective dosage of the GLP-1 molecule is in the range of about 5 to about 200 μg per day.

13. The method of claim 11 wherein the effective dosage of the GLP-1 molecule is in the range of about 20 to about 100 μg per day.

14. The method of claim 11 wherein the effective dosage of the GLP-1 molecule is in the range of about 30 to about 50 μg per day.

15. The method of claim 11 wherein the effective dosage of pioglitazone or rosiglitazone is in the range of about 0.1 mg to about 200 mg per day.

16. The method of claim 11 wherein the effective dosage of pioglitazone or rosiglitazone is in the range of about 50 mg to about 200 mg per day.

17. The method of claim [4] *1* wherein the GLP-1 molecule comprises Valine, Glycine, Threonine, or Methionine at position 8.

18. The method of claim 17 wherein the effective dosage of the GLP-1 molecule is in the range of about 5 to about 200 μg per day.

19. The method of claim 17 wherein the effective dosage of the GLP-1 molecule is in the range of about 20 to about 100 μg per day.

20. The method of claim 17 wherein the effective dosage of the GLP-1 molecule is in the range of about 30 to about 50 μg per day.

21. The method of claim 17 wherein the effective dosage of pioglitazone or rosiglitazone is in the range of about 0.1 mg to about 200 mg per day.

22. The method of claim 17 wherein the effective dosage of pioglitazone or rosiglitazone is in the range of about 50 mg to about 200 mg per day.

23. The method of claim [4] *1* wherein the effective dosage of the GLP-1 molecule is in the range of about 5 to about 200 μg per day.

24. The method of claim [4] *1* wherein the effective dosage of the GLP-1 molecule is in the range of about 20 to about 100 μg per day.

25. The method of claim [4] *1* wherein the effective dosage of the GLP-1 molecule is in the range of about 30 to about 50 μg per day.

26. The method of claim [4] *1* wherein the effective dosage of pioglitazone or rosiglitazone is in the range of about 0.1 mg to about 200 mg per day.

27. The method of claim [4] *1* wherein the effective dosage of pioglitazone or rosiglitazone is in the range of about 50 mg to about 200 mg per day.

[28. The method of claim 1 wherein the effective dosage of the GLP-1 agonist is in the range of about 5 to about 200 μg per day.]

[29. The method of claim 1 wherein the effective dosage of the GLP-1 agonist is in the range of about 20 to about 100 μg per day.]

[30. The method of claim 1 wherein the effective dosage of the GLP-1 agonist is in the range of about 30 to about 50 μg per day.]

[31. The method of claim 1 wherein the effective dosage of pioglitazone or rosiglitazone is in the range of about 0.1 mg to about 200 mg per day.]

[32. The method of claim 1 wherein the effective dosage of pioglitazone or rosiglitazone is in the range of about 50 mg to about 200 mg per day.]

33. The method of claim 1 wherein the GLP-1 [agonist] *molecule* is administered as a composition comprising a GLP-1 molecule at a concentration of between $10^{-12}$ M and $10^{-5}$ M.

34. The method of claim 1 wherein the GLP-1 [agonist] *molecule* is administered as a controlled release preparation.

* * * * *